United States Patent [19]

Little

[11] 4,214,804
[45] Jul. 29, 1980

[54] PRESS FIT ELECTRICAL CONNECTION APPARATUS

[75] Inventor: Richard L. Little, Minneapolis, Minn.

[73] Assignee: Daig Corporation, Minnetonka, Minn.

[21] Appl. No.: 945,113

[22] Filed: Sep. 25, 1978

[51] Int. Cl.² ............................................. H01R 11/32
[52] U.S. Cl. ................................. 339/183; 128/419 P
[58] Field of Search ......... 339/182 R, 182 L, 182 RS, 339/182 T, 183; 128/404, 419 P

[56] References Cited

U.S. PATENT DOCUMENTS

| 3,291,926 | 12/1966 | Nelson | 339/182 RS |
| 3,769,984 | 11/1973 | Muench | 128/419 P X |
| 4,027,678 | 6/1977 | Van Oostveen | 128/419 P |
| 4,046,151 | 9/1977 | Rose | 128/404 |
| 4,135,518 | 1/1979 | Dutcher | 128/404 X |

Primary Examiner—Joseph H. McGlynn
Assistant Examiner—John S. Brown
Attorney, Agent, or Firm—Clayton R. Johnson

[57] ABSTRACT

A pacemaker bipolar lead assembly, for being electrically connected to a pulse generator to transmit electrical pulses into a heart, that includes a pair of wire conductor spring coils electrically connected to conductor pins, the first coil being electrically connected to a tip electrode and the second coil being electrically connected to a ring electrode. An internal ring having an outwardly facing groove is press fitted within the ring electrode with the second coil extending through the groove to retain the second coil in electrical conducting relationship with the ring electrode. Electrical insulation is provided on the coils and the conductor pins except for one end portions of the pins, the part of the second coil that is in electrical contact with the ring electrode and the juncture of the first coil with the tip electrode. An insulated portion of the first coil extends through the internal ring.

3 Claims, 3 Drawing Figures

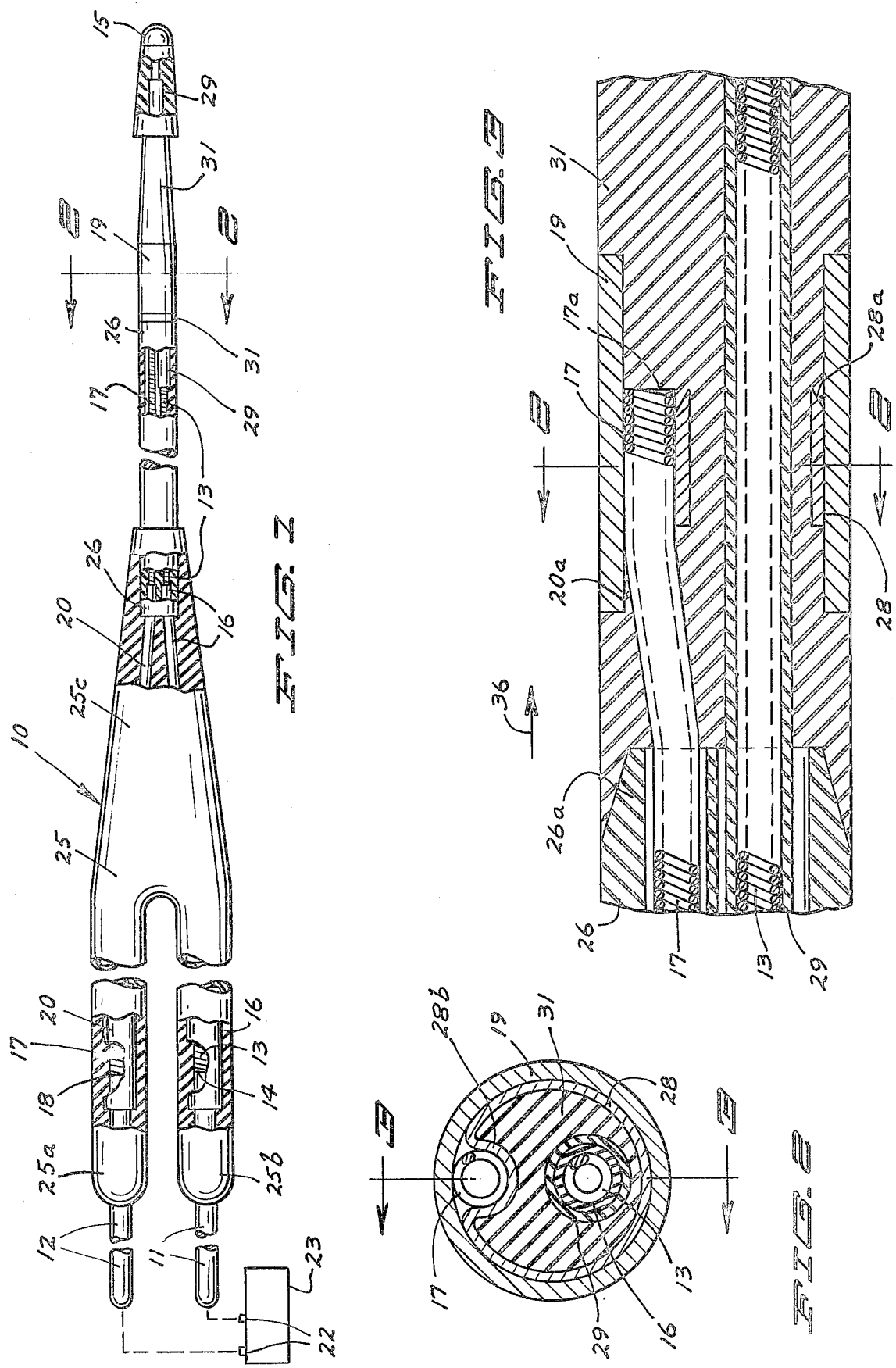

PRESS FIT ELECTRICAL CONNECTION APPARATUS

BACKGROUND OF THE INVENTION

A pacemaker bipolar lead assembly for being electrically connected to a pulse generator implanted in a human body to transmit pulses to a heart.

In prior art pacemaker bipolar lead assemblies the welding of one end portion of an electrically conductive wire coil to the ring electrode has resulted in annealing of the wire of the coil and degradation of the wire and ring. Further, when leakage of body fluids occurs so that the fluid contacts the weld, corrosion occurs adjacent the weld at places where the fluids contact the electrically conductive metal. The above is undesirable. In order to overcome or minimize problems such as the above, this invention has been made.

SUMMARY OF THE INVENTION

A pacemaker bipolar lead assembly for transmitting electrical pulses from a pulse generator to a heart that includes a first coil electrically connecting a connector pin to a tip electrode, a second coil electrically connected to a second connector pin, a ring electrode and means in press fitting relationship with the ring electrode to retain the second coil in electrical conductive relationship with the ring electrode.

One of the objects of this invention is to provide new and novel means for retaining one end portion of an electrically conductive coil of a pacemaker lead assembly in electrically conductive relationship with a ring electrode. A further object of the invention is to provide a new and novel means that results in a relative reliable electrical connection between an electrically conductive coil and a ring electrode of a pacemaker lead assembly.

BRIEF DESCRIPTION OF THE DRAWINGS

FIG. 1 is a diagrammatic showing of a pulse generator and a plan view of a pacemaker lead assembly of this invention, intermediate portions of the assembly not being shown and other portions being broken away to show various structural features;

FIG. 2 is a transverse cross sectional view generally taken along the line and in the direction of the arrows 2—2 of FIG. 3 to show the internal ring press fitted within the ring electrode to retain one of the wire coils in electrically conductive relationship with the ring electrode; and FIG. 3 is a fragmentary longitudinal cross sectional view generally taken along the line and in the direction of arrows 3—3 of FIG. 2 to further illustrate the structural relationship between the coils, ring electrode and internal ring.

Referring now to the drawings, a bifurcated bipolar lead assembly, generally designated 10, which is implantable in a human body to extend into a heart, includes a pair of connector pins for being electrically connected with a pair of terminals 22 of a pulse generator 23 that provides pulses for maintaining a desired rate of heart beats. An axially elongated coil spring 13 has one end electrically connected at 14 to one end of pin 11, while a similar coil spring 17 of a shorter length than spring 13 has one end electrically connected at 18 to one end of pin 12. The opposite end of coil spring 13 is electrically connected to tip electrode 15 in a conventional manner, while the opposite end of coil spring 17 is electrically connected to an electrically conductive metal ring electrode 19 in a manner more fully set forth hereinafter. A generally tubular layer of electrical insulation 16 surrounds the end portion of pin 11 adjacent coil 13 and coil 13 (not individual helices) from the electrical connection 14 to just inside of the adjacent end of one lumen of an elongated flexible bilumen plastic tube 26, while a layer of electrical insulation 20 surrounds the end portion of pin 12 adjacent coil 17 and coil 17 from electrical connection 18 to just inside of the other lumen of tube 26.

Axially intermediate the pins 11 and 12, and the ring electrode, the coils 13, 17 extend through bilumen tube 26, one end of the tube being adjacent, but spaced from the ring electrode by a fraction of an inch while the opposite end of the tube is more closely adjacent to, but remotely spaced from the pins 11, 12. The said opposite end of the tube is embedded in one end portion of leg 25c of a plastic bifurcated junction member (somewhat Y-shaped) 25. Junction member 25 also includes bifurcated elongated legs 25a, 25b, one end portion of pin 12 and the end portion of insulation 20 that extends from leg 25c to pin 12 being embedded in leg 25a. The one end portion of pin 11 and the end portion of insulation 16 that extends from leg 25c to pin 11 is embedded in leg 25b. Junction member 25 advantageously is made of silicone rubber.

In accordance with this invention there is provided an electrically conductive metal internal ring 28 to maintain one end of coil 17 in electrical contact with the internal surface of ring electrode 19. The outer diameter of the internal ring, except for tapered portion 28a and grooved portion 28b, is of a dimension that the internal ring will provide a press fit with the ring electrode when the internal ring is pushed into the ring electrode. The one end portion 28a of the internal ring is beveled around the outer periphery of the ring to provide an outer tapered surface that extends toward the opposite end in a radial outward direction. The minimum diameter of the beveled portion, at other than grooved portion 28b is less than the inner diameter of the ring electrode to facilitate pushing the internal ring into the ring electrode. The axial length of the internal ring may be substantially less than that of the ring electrode, for example about ½.

As viewed in transverse cross section, FIG. 2, the major part of the grooved portion is of a circular arcuate configuration, i.e. other than at the junctures to the nongrooved part of the ring. The radius of curvature of the outer surface of the grooved portion (the surface that faces the inner surface of the ring electrode) is slightly less than the outer radius of the helices of the coil 17 in a relaxed condition. The outer surface of grooved portion extends arcuately through an angle that is typically, though not necessarily, a little less than 180°. Additionally the maximum radial spacing of the internal ring outer surface from the part of ring electrode inner surface that the grooved portion 28b opens to is less than the maximum outer diameter of the helices of coil 17 in a relaxed condition. As a result when the end portion 17a of the coil 17 extends through grooved portion 28b with the internal ring located within the electrode ring, coil portion 17a is compressed such the angle of the helices of portion 17a with the central axis of the coil is less than that of the noncompressed part of the coil. This firmly retains coil portion 17a in electrical contact with the inner surface of electrode ring and the outer surface of the grooved portion of the internal ring. Thus electricity is conducted directly from coil portion 17a to the ring electrode along a substantial part of the axial length of the ring electrode and indirectly from the portion 17a through the internal ring to the ring electrode.

The coil 13 has an insulating layer (sleeve) 29 which extends through the inner ring 28, and extends from closely adjacent the tip electrode to a position within tube 26 that is remote from junction member 25.

With the sleeve 29 extended through the internal ring and coil end portion 17a extended into the electrode ring, the internal ring is forced in the direction of arrow 36 into the ring electrode with its tapered end 28 extended thereinto first and the coil 17 extending into the grooved portion 28b. When the internal ring is in place as shown in FIG. 3 the bare wire of coil end portion abuts against both the ring electrode and the internal ring along at least the axial length of the nontapered part of the internal ring. The coil spring end portion 17a has a terminal end more remote from pins 11, 12 than the end of the internal ring that is most closely adjacent said pins and that is more closely adjacent the opposite second end portion of the internal ring than the internal ring first end. Advantageously end portion 17a extends axially a short distance to the right of the internal ring as viewed in FIG. 3 whereby the terminal end portion of the coil is not compressed. This more firmly retains the coil in place between the ring electrode and the ring 28.

After the coils are connected to the electrodes and pins and sleeve 29 and tube 26 are in place, plastic is molded to form bifurcated member 25. Additionally, a molded plastic section 31 is formed to extend over tapered end portion 26a and through the rings 19,28 to the tip electrode to block liquid seepage into the ring electrode.

Section 31, member 25 and the tube 26 may be made of silicone rubber. The portion of assembly 10 from bifurcated member 25 to the tip electrode is of sufficient flexibility so that the assembly can be inserted through a blood vessel and into the heart to conduct a pulse from a pulse generator located in the body to the heart.

Preferably the ring electrode and internal ring are of the same metal or metal alloy. By using the internal ring, the coil 17 is retained in electrical contact with the ring electrode and no heat is applied to make the electrical connection. As a result, annealing of the wire coil and degradation of the wire and ring electrode does not occur such as occurs when the coil spring is welded to the ring electrode in a conventional manner. Additionally, the internal ring in being pushed into position crimps the part of the coil that abuts against the inner surface of the ring electrode to form a more reliable electrical connection than is obtained by welding procedures that are normally used. With reference thereto it is to be noted that there is no reasonable way of checking the sufficiency of such a weld without damage to the lead assembly.

In the event there should be some separation of the molded member 31 from the electrode ring when the lead assembly is in the body whereby there is some leakage of body fluids so that the body fluids contacts the area of electrical connection of coil 17 to the electrode ring, the electrical connection obtained by using the internal ring of this invention is less affected by resulting corrosion than by using a usually conventional weld type connection.

What is claimed is:

1. For transmitting an electrical pulse from a pair of terminals of a pulse generator to a heart, a bipolar lead assembly comprising a first and a second connector pin adapted for being electrically connected to the terminals of a pulse generator, a tip electrode, a ring electrode having an inner surface, an elongated first electric conduit electrically connecting the first pin to the tip electrode, an elongated second electric conduit having a first end portion electrically connected to the second pin, and a second end portion extended into the ring electrode, said second end portion being a coil spring end portion, and means extending into the ring electrode in press fitting relationship thereto for retaining the coil spring end portion in electrical conductive relationship with the ring electrode, said means comprising an internal ring of electrically conductive metal having an exterior surface portion in electrically conductive relationship with the ring electrode inner surface and said coil spring end portion, the internal ring having a portion having an exterior groove opening to the ring electrode interior surface, the major part of the grooved portion being of a circular arcuate configuration and having an outer surface facing the ring electrode, the maximum radial spacing of the internal ring outer surface from the part of the ring electrode interior surface that the grooved portion open to being less than the maximum outer diameter of the helices of the coil spring end portion in a relaxed condition.

2. The apparatus of claim 1 further characterized in that the outer surface of the circular part of the grooved portion of the internal ring is of a radius of curvature that is slightly less than the outer radius of the helices of the coil spring in a relaxed condition.

3. In an electric lead assembly, an elongated electrically conductive pin having a bare first end portion and a second end portion, a ring electrode remotely spaced from the pin and having an inner surface, an axially elongated, electrically conductive coil spring having a first end portion electrically connected to the pin second end portion and a second end portion extended into the ring electrode in electrically conductive relationship therewith, and an electrically conductive internal ring in press fitted relationship with the ring electrode for retaining the coil spring in electrically conductive relationship with the ring electrode, the internal ring having an exterior surface portion in abutting relationship with the ring electrode interior surface and a portion having an exterior groove opening to the ring electrode interior surface, the coil spring second end portion extending into the groove in a compressed condition between the grooved portion and the electrode ring interior surface, and flexible electrical insulating means surrounding the pin second end portion and the coil spring from the pin to the ring electrode, the internal ring having a first end and a second end portion that is more remote from pin than its first end and the coil spring second end portion having a terminal end that is more remote from the pin than the internal ring first end and more closely adjacent the internal ring second end portion than the internal ring first end.

* * * * *